United States Patent [19]

Petrovsky et al.

[11] Patent Number: 6,097,975

[45] Date of Patent: Aug. 1, 2000

[54] APPARATUS AND METHOD FOR NONINVASIVE GLUCOSE MEASUREMENT

[75] Inventors: Gury Timofeevich Petrovsky; Michail Davidovich Slavin; Lubov Aleksandrovna Slavina; Natalia Leonidovna Izvarina, all of St. Petersburg, Russian Federation; Miroslav Orestes Pankevich, Beachwood, Ohio

[73] Assignee: BioSensor, Inc., Atlanta, Ga.

[21] Appl. No.: 09/076,795

[22] Filed: May 13, 1998

[51] Int. Cl.$^7$ ........................................................ A61B 5/00
[52] U.S. Cl. ............................................. 600/316; 600/322
[58] Field of Search ..................................... 600/310, 316, 600/322, 473, 476, 326; 356/39

[56] References Cited

U.S. PATENT DOCUMENTS

| | | |
|---|---|---|
| 3,958,560 | 5/1976 | March . |
| 4,014,321 | 3/1977 | March . |
| 4,655,225 | 4/1987 | Dähne et al. . |
| 5,028,787 | 7/1991 | Rosenthal et al. . |
| 5,070,874 | 12/1991 | Barnes et al. . |
| 5,077,476 | 12/1991 | Rosenthal . |
| 5,086,229 | 2/1992 | Rosenthal et al. . |
| 5,119,819 | 6/1992 | Thomas et al. . |
| 5,139,023 | 8/1992 | Stanley et al. . |
| 5,140,985 | 8/1992 | Schroeder et al. . |
| 5,243,983 | 9/1993 | Tarr et al. . |
| 5,267,152 | 11/1993 | Yang et al. . |
| 5,277,181 | 1/1994 | Mendelson et al. . |
| 5,313,941 | 5/1994 | Braig et al. . |
| 5,361,758 | 11/1994 | Hall et al. . |
| 5,370,114 | 12/1994 | Wong et al. . |
| 5,383,452 | 1/1995 | Buchert . |
| 5,398,681 | 3/1995 | Kupershmidt . |
| 5,424,544 | 6/1995 | Shelton et al. . |
| 5,433,197 | 7/1995 | Stark . |
| 5,434,412 | 7/1995 | Sodickson et al. . |
| 5,448,992 | 9/1995 | Kupershmidt . |
| 5,459,317 | 10/1995 | Small et al. . |
| 5,529,755 | 6/1996 | Higashio et al. . |
| 5,533,509 | 7/1996 | Koashi et al. ........................... 600/316 |
| 5,553,509 | 9/1996 | Somes . |
| 5,553,613 | 9/1996 | Parker . |
| 5,601,079 | 2/1997 | Wong et al. . |

OTHER PUBLICATIONS

Gifford, R.S. and Bartnik, D.J., "Using Optical Sensors to Measure Arterial Blood Gases," *Optics & Photonics News*, Mar. 1998, pp. 28–30, 32.

Heise, H.M., "Non–Invasive Monitoring of Metabolites Using Near Infrared Spectroscopy: State of the Art," *Horm. Metab. Res.*, 28:527–534 (1996).

Heise, H.M., Marbach, R., Koschinsky T., and Gries, F.A., "Noninvasive Blood Glucose Sensors Based on Near–Infrared Spectroscopy," *Artificial Organs*, 18(6):439–447 (1994).

Lakowicz, J.R. and Szmacinski, H., "Emerging Biomedical Applications of Time–Resolved Fluorescence," Center for Fluorescence Spectroscopy, Dept. of Biochemistry, Univ. of Maryland, at Baltimore, School of Medicine, 108 N. Greene Street, Baltimore, MD 21201, pp. 362–365.

Reiss, S.M., "Glucose– and Blood–Monitoring Systems Vie for Top Spot," *Biophotonics International*, May/Jun. 1997, pp. 43–45.

Robinson, K., "Noninvasive Methods Hover on Horizon," *Biophotonics International*, May/Jun. 1998, pp. 48–49, 51–52.

*Primary Examiner*—Eric F. Winakur
*Attorney, Agent, or Firm*—Finnegan, Henderson, Farabow, Garrett & Dunner, L.L.P.

[57] ABSTRACT

An apparatus and method for noninvasively measuring blood glucose concentration. The apparatus disclosed uses light pulses directed onto a patient's skin and reflected back from the patient to measure blood glucose. Reflected light is passed through light filters that transmit a narrow bandwidth of light within a range of wavelengths that is absorbed by glucose and then measured. Unreflected light is passed through identical light filters and also measured. The two measurements are then compared and used to calculate the patient's blood glucose concentration.

20 Claims, 6 Drawing Sheets

APPARATUS AND METHOD FOR NONINVASIVE GLUCOSE MEASUREMENT

BACKGROUND OF THE INVENTION

More than 16 million people in the United States are afflicted with diabetes mellitus or have a predisposition to diabetes, and more than 750 thousand people are registered annually as diabetics. The medical complications associated with diabetes are quite serious, including increased risk of kidney, eye, nerve, and heart disease. To control their condition, diabetics must control their blood sugar levels by selecting proper nutrition and, in the more serious Type I condition, by administering insulin. To help guide their nutrition and their regimen of insulin injections, diabetics must also measure their sugar levels several times a day.

At present, all portable devices for measuring blood sugar require puncturing the fingertip to obtain a blood sample. The blood sample is then placed on a test strip that indicates the glucose concentration. An example is the ONE TOUCH® glucose meter sold by the LifeScan Co. These devices are very compact and reasonably accurate, but puncturing the fingertip to obtain a blood sample is inconvenient and painful and poses a risk of infection. No commercial alternatives are available.

A number of attempts have been made to measure blood sugar concentration noninvasively by measuring tissue absorption of light radiation in the near infrared energy spectrum—approximately 650 nm to 2700 nm. Various attempts are described in U.S. Pat. No. 4,655,225 (Dahne), U.S. Pat. No. 5,070,874 (Barnes), U.S. Pat. No. 5,077,476 (Rosenthal), U.S. Pat. No. 5,086,229 (Rosenthal), U.S. Pat. 5,277,181 (Mendelson), U.S. Pat. No. 5,361,758 (Hall), U.S. Pat. No. 5,459,317 (Small), and U.S. Pat. No. 5,529,755 (Higashio).

Some of these prior patents, such as U.S. Pat. Nos. 5,070,874, 5,077,476, and 5,086,229, disclose only using wavelengths less than 2000 nm, most of which do not penetrate well through human skin. Others of these patents, such as U.S. Pat. Nos. 4,655,225, 5,277,181, 5,361,758, 5,459,317, and 5,529,755, disclose applying multiple wavelengths of energy and require complicated apparatus, such as a continuous wide-band radiation source, which restricts the ability to construct a compact portable unit from these designs.

U.S. Pat. No. 5,313,941 (Braig) discloses using a radiation source of long infrared energy, specifically from 2000–20,000 nm, applied in short bursts to avoid patient discomfort and/or burning of tissue. In a preferred embodiment, a wavelength of approximately 9100 nm is used to detect the concentration of glucose, and a wavelength of approximately 10,500 nm is used as a reference. The source of infrared energy is a heating element that radiates a broad spectrum of energy, and a mechanical shutter regulates the flow of energy into short bursts. In addition, the mechanical shutter is synchronized with the patient's systolic and diastolic phases of the cardiac cycle. A disadvantage of this method is that sophisticated filters and photodetectors are needed to measure the signals in these spectral regions. Another disadvantage is that the high energy source requires a large power supply, which restricts the ability to construct a compact and portable unit.

U.S. Pat. Nos. 5,398,681 and 5,448,992 describe a polarizing method to measure blood sugar concentrations. Disadvantages of these methods include but are not limited to the need for many elements, fine adjustments, and precise techniques to fix changes in the plane of polarization when measuring blood-sugar/glucose concentrations. Another disadvantage is that the negative influence of other blood constituents is not excluded in the measurements. An apparatus of this nature could not be constructed to form a compact and portable unit.

In short, to date, all attempts have failed to replace the current methods of measuring blood glucose concentration with a noninvasive glucose analyzer that is accurate, convenient, portable, and reliable.

SUMMARY OF THE INVENTION

An objective of the invention is to provide an apparatus and method for noninvasively measuring blood glucose concentration accurately and conveniently. A further objective of the invention is to provide an apparatus for noninvasively measuring blood glucose concentration that is portable and inexpensive. A more specific objective is to provide a photometric method for noninvasively measuring blood glucose concentration in vivo in which a pulse of light is projected onto a selected area of the body rich in blood vessels (such as the inner wrist, elbow or ear lobe), transmitted through the skin, tissues, and blood vessels, partially absorbed by glucose in the blood, and partially scattered, diffused, and reflected off irradiated structures (such as bone surfaces or internal surfaces of blood vessels) and back through the blood vessels, tissues, and skin. The luminous energy of the reflected light (including scattered and diffused light) is then collected by a receiving detector, converted to an electrical signal proportional to the glucose concentration in the blood of the subject, and analyzed. Additional objectives of the invention will be set forth in part in the description that follows or will be obvious from the description.

To achieve the objectives of the invention, as embodied and broadly described herein, the invention comprises an apparatus for noninvasively measuring the glucose concentration in the blood of a patient comprising a light source, a first fiber optic unit, a test channel, a second fiber optic unit, a reference channel, and a processing unit. The first fiber optic unit transports light pulses to the skin of a patient, receives light reflected back from the patient, and transports the reflected light to the test channel. The test channel comprises a light filter that transmits a narrow bandwidth of light within a range of wavelengths that is absorbed by glucose, a photodetector that measures the light passing the light filter, a pulse amplifier, and an analog-to-digital converter. The test channel measures the intensity of the reflected light at the desired wavelengths. The second fiber optic unit transports light pulses directly from the light source to the reference channel, which comprises a light filter, a photodetector, a pulse amplifier, and an analog-to-digital converter identical to the corresponding elements in the test channel. The reference channel measures the intensity of the light from the light source at the desired wavelengths. The processing unit then compares the output of the test channel to the output of the reference channel to quantify the intensity of light absorbed by the glucose in the blood of the patent. This measurement can then be converted into a measurement of glucose concentration. In preferred embodiments, the light filters may transmit light having a bandwidth of about 20 nm or less within a range of wavelengths of between about 1550 nm to 1700 nm or between about 2050 nm to 2400 nm, more preferably between about 2080 to 2200 nm. In a most preferred embodiment, the first and second fiber optic units comprise pure silica glass core fiber or doped silica glass core fiber.

The invention also comprises an embodiment an apparatus for noninvasively measuring the glucose concentration in the blood of a patient in which sequential light pulses from the first and second fiber optic units pass through the same light filter and photodetector. This embodiment comprises a light source; a light filter that transmits a narrow bandwidth of light within a range of wavelengths that is absorbed by glucose; a first fiber optic unit that transports light pulses from the light source to the skin of a patient, receives light reflected back from the patient, and transports the reflected light to the light filter; a second fiber optic unit that transports light pulses directly from the light source to the light filter; a photodetector that measures the light passing the light filter; and a processing unit that compares the intensity of the reflected light passing through the light filter to the intensity of the light directly from the light source to quantify the intensity of light absorbed by the glucose in the blood of the patient. In a preferred embodiment, the light filter transmits light having a bandwidth of about 20 nm or less and within a range of wavelengths of between about 1550 nm to 1700 nm or between about 2050 nm and 2400 nm, more preferably between about 2080 nm to 2200 nm. In a most preferred embodiment, the first and second fiber optic units comprise pure silica glass core fiber or doped silica glass core fiber.

The invention also comprises a method for noninvasively measuring the glucose concentration in the blood of a patient, comprising projecting a pulse of light onto the patient's skin, measuring the intensity of light reflected from the patient over a narrow bandwidth within a range of wavelengths that is absorbed by glucose, measuring the intensity of light projected onto the patient's skin over the same bandwidth and wavelengths as for the reflected light, and comparing the measurements to quantify the intensity of light absorbed by the glucose in the blood of the patient. In one embodiment of this method, the light projected onto the patient's skin has a narrow bandwidth and is within a range of wavelengths of between about 1550 nm to 1700 nm or between about 2050 nm and 2400 nm. More preferably, the light projected onto the patient's skin has a bandwidth of about 20 nm or less and is within a range of wavelengths of between about 2080 nm to 2200 nm.

The invention further comprises a method for noninvasively measuring the glucose concentration in the blood of a patient comprising generating a pulse of light, projecting a first portion of the pulse of light onto the patient's skin, passing the light reflected from the patient through a first light filter that transmits a narrow bandwidth of light within a range of wavelengths that is absorbed by glucose, passing a second portion of the pulse of light through a second light filter identical to the first light filter, measuring the intensity of the light passing through the first and second light filters, and comparing the intensity of light passing through the first light filter to the intensity of light passing through the second light filter to quantify the intensity of the light absorbed by the glucose in the blood of the patient. In preferred embodiments, the light filters transmit light having a bandwidth of about 20 nm or less within a range of wavelengths between about 1550 nm to 1700 nm or between about 2050 nm to 2400 nm, more preferably between about 2080 nm to 2200 nm. In a most preferred embodiment, first portion of the pulse of light is projected onto the skin by a projection device comprising a light source, a detector, and a fiber optic bundle. The projection device can be placed on the lateral side of the patient's ear lobe, and a reflective device can be placed on the medial side of the patient's ear lobe and aligned parallel to a window on the fiber optic device so that the maximum signal is reflected into the window.

DESCRIPTION OF PREFERRED EMBODIMENTS

Some preferred and exemplary embodiments of the invention, which are also illustrated in the accompanying drawings, are described below.

Figure 1:
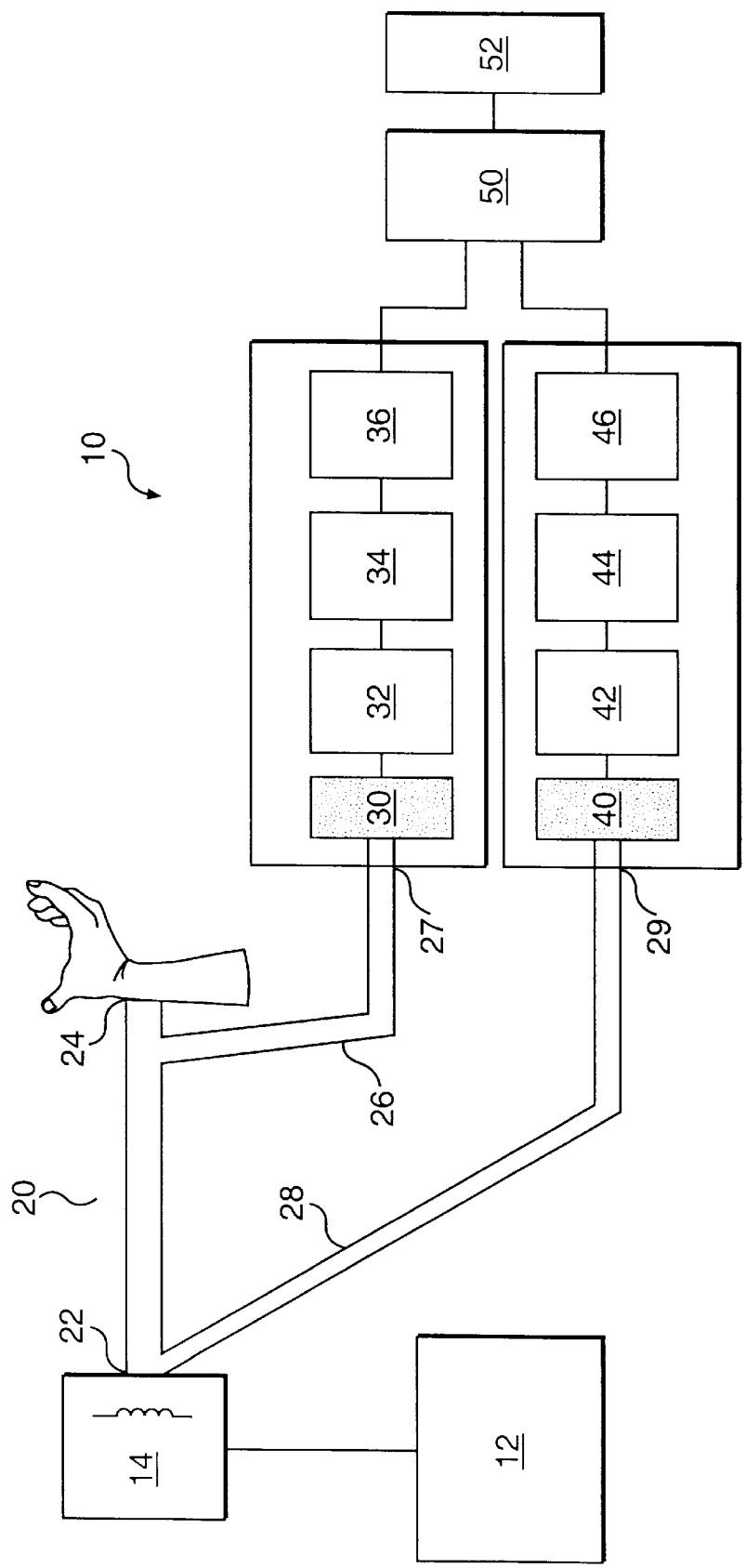
FIG. 1 is a block diagram of an apparatus according to one embodiment of the present invention.
Figure 2A:
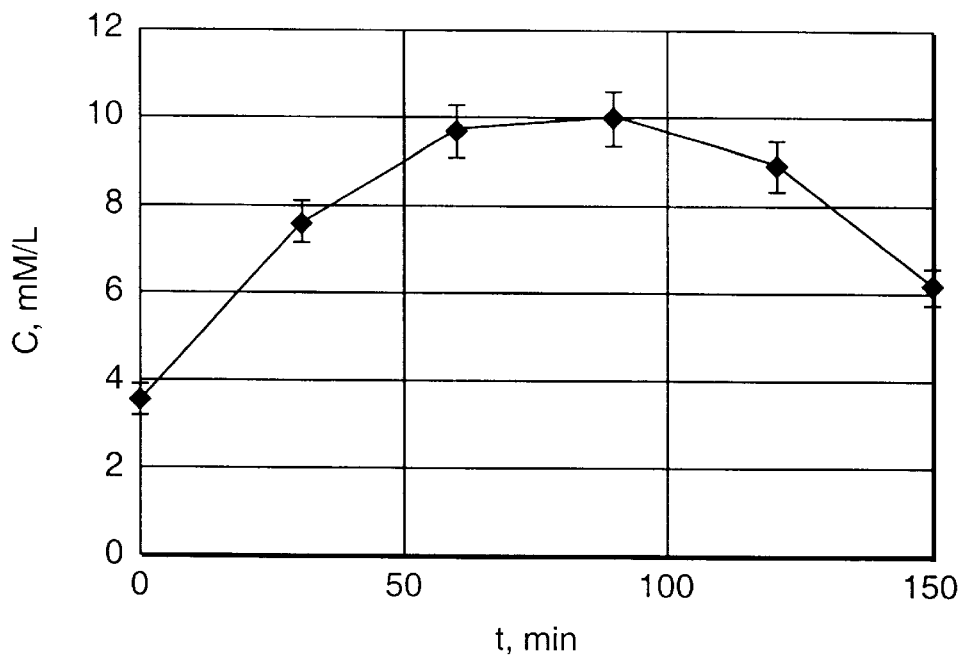
FIG. 2a is a chart depicting blood glucose content in a patient analyzed by a biochemical method.
Figure 2B:
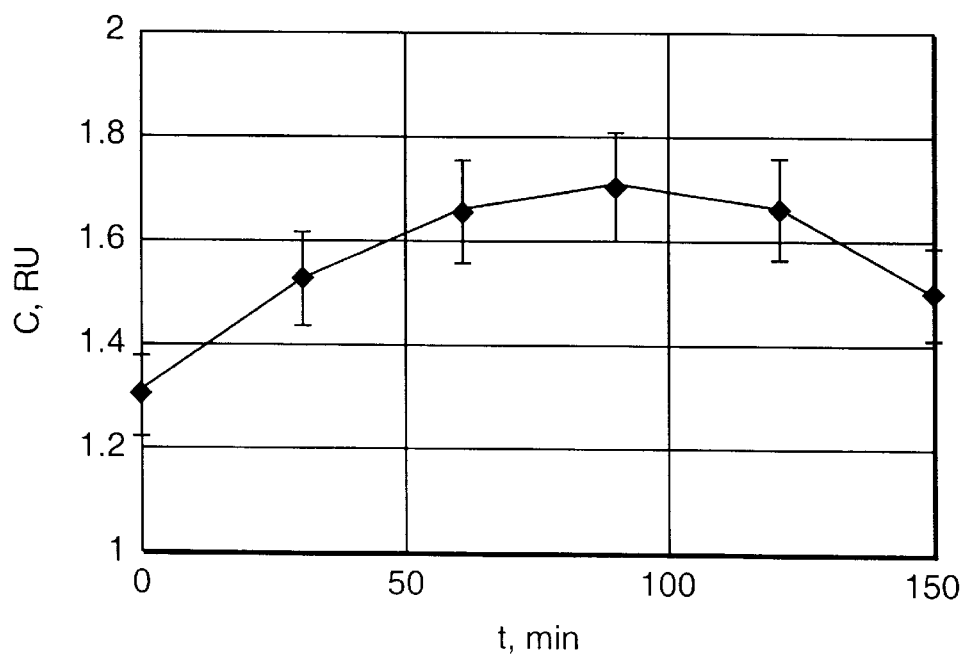
FIG. 2b is a chart depicting blood glucose content in the same patient analyzed using the present invention.
Figure 3A:
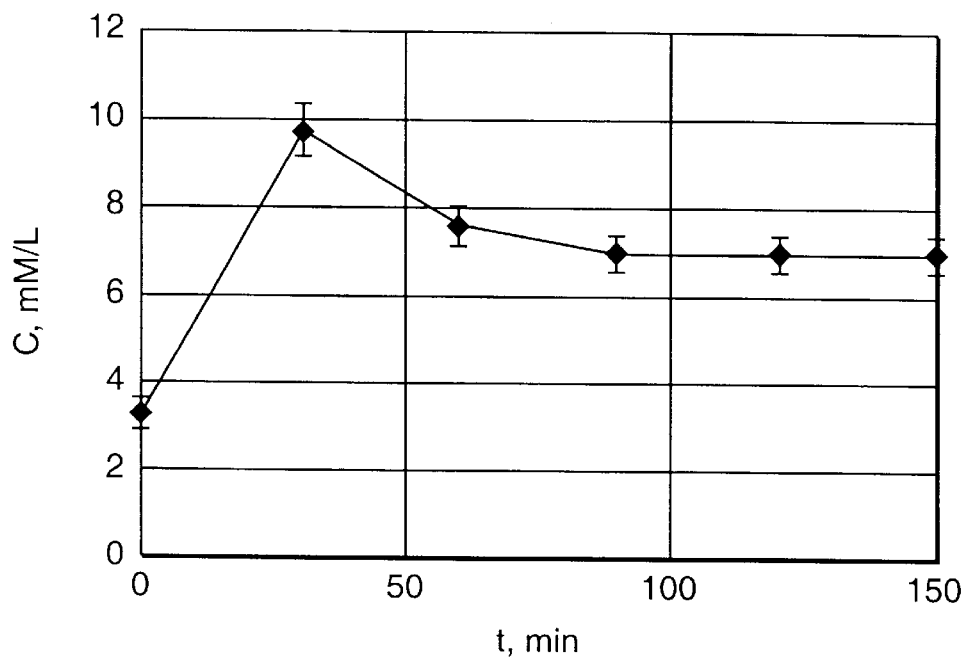
FIG. 3a is a chart depicting blood glucose content in a patient analyzed by a biochemical method.
Figure 3B:
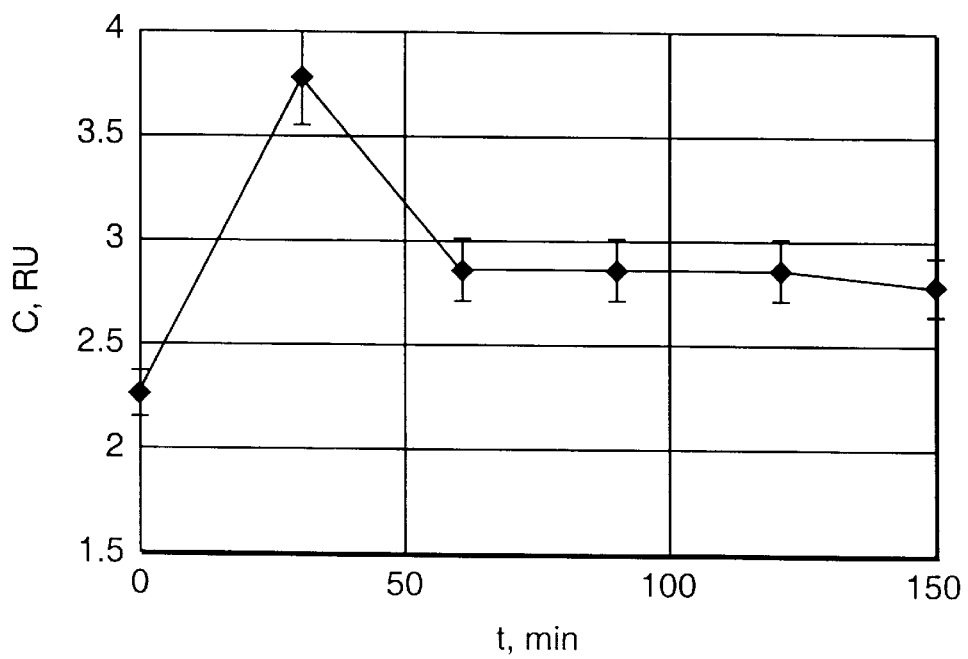
FIG. 3b is a chart depicting blood glucose content in the same patient analyzed using the present invention.
Figure 4A:
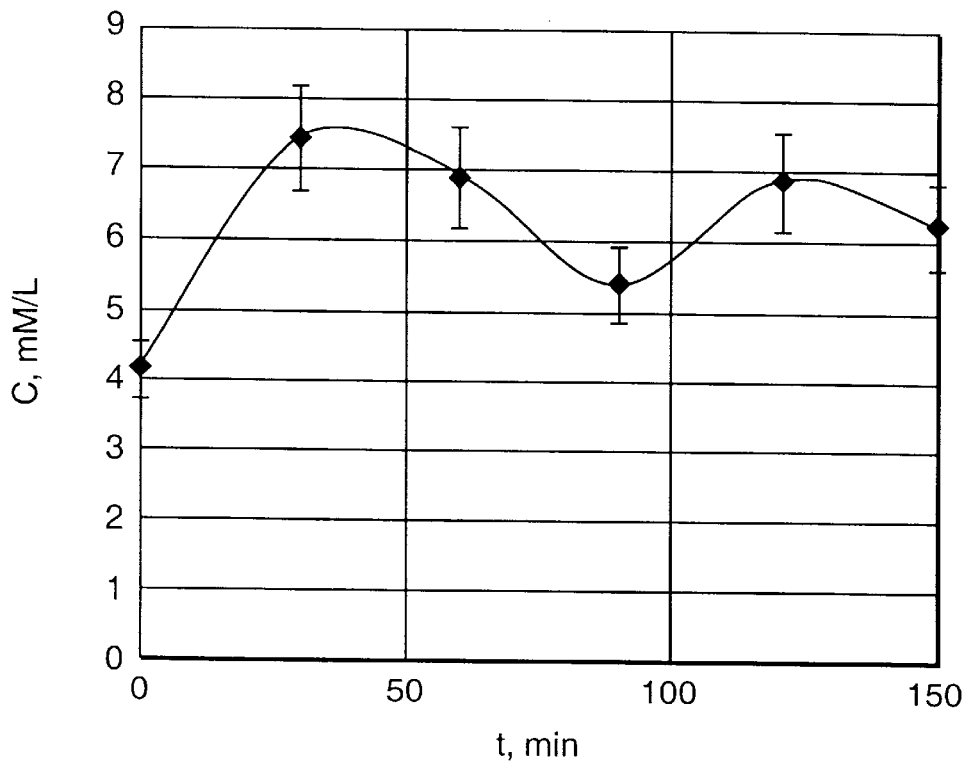
FIG. 4a is a chart depicting blood glucose content in a patient analyzed by a biochemical method.
Figure 4B:
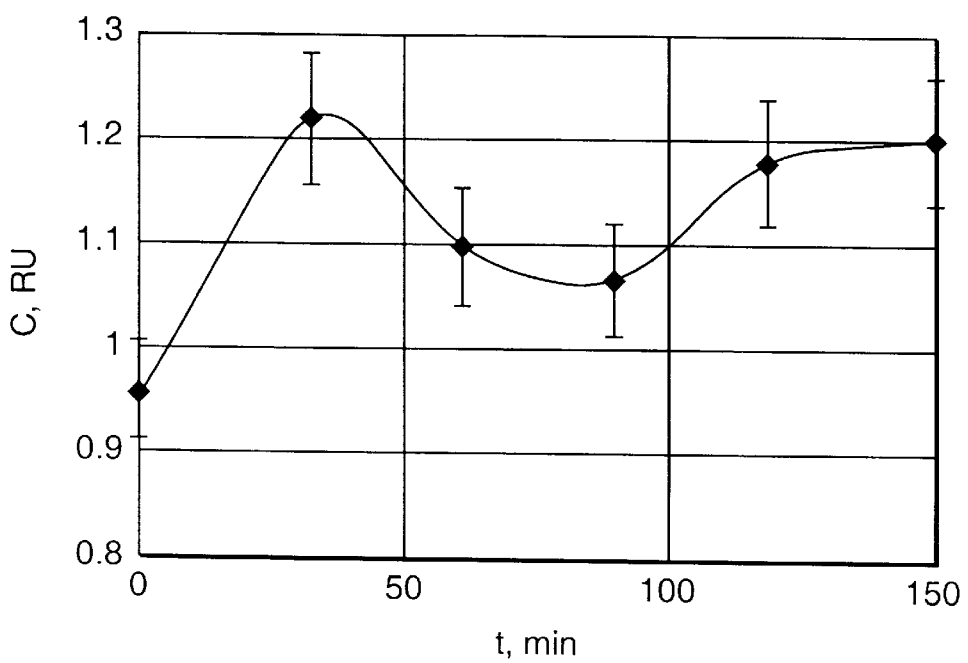
FIG. 4b is a chart depicting blood glucose content in the same patient analyzed using the present invention.
Figure 5A:
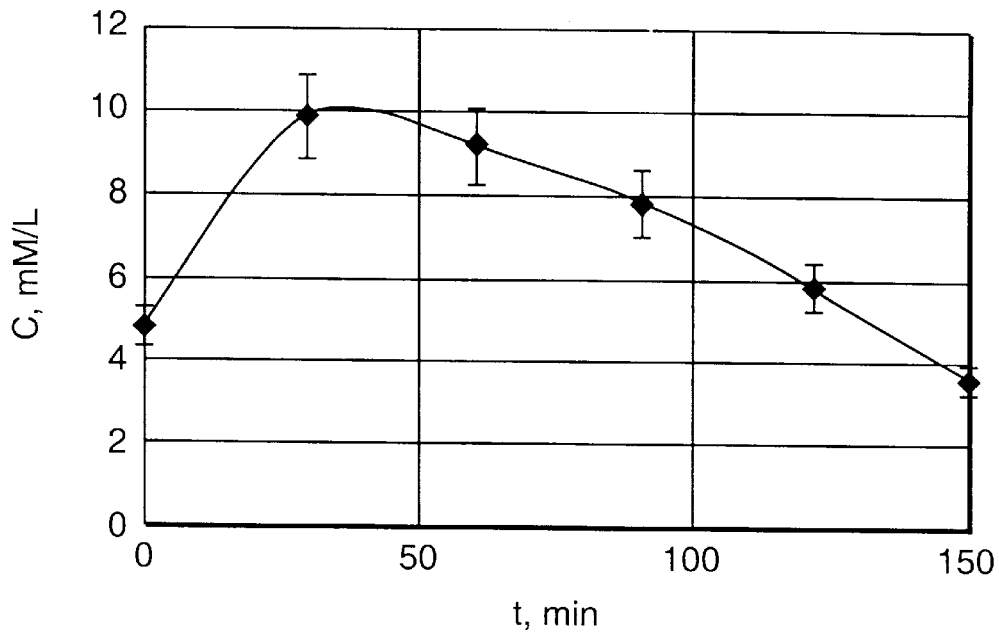
FIG. 5a is a chart depicting blood glucose content in a patient analyzed by a biochemical method.
Figure 5B:
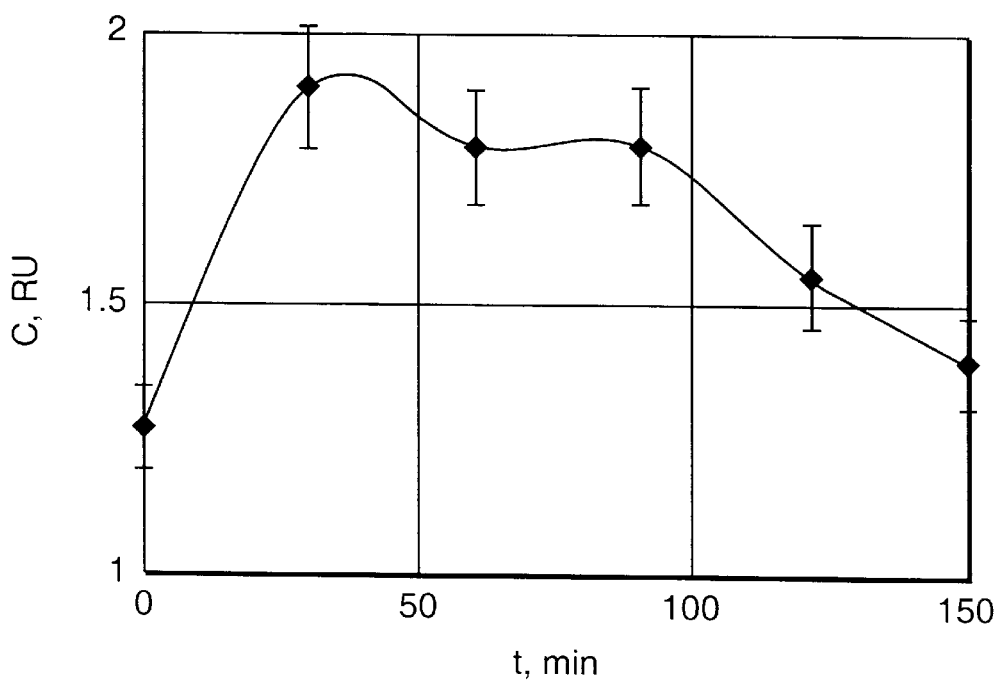
FIG. 5b is a chart depicting blood glucose content in the same patient analyzed using the present invention.
Figure 6A:
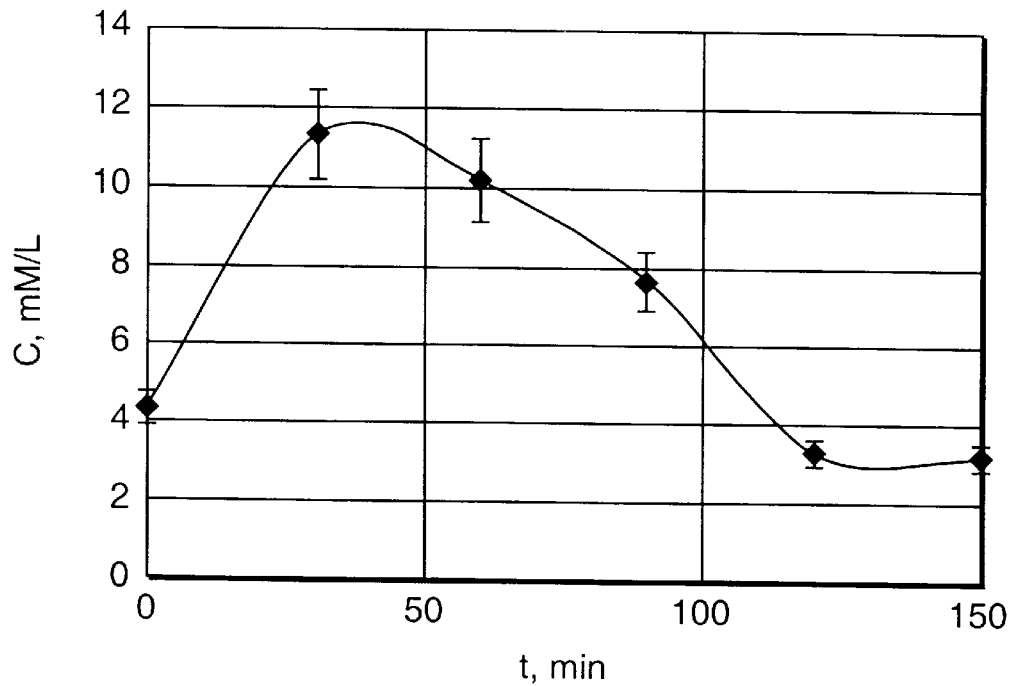
FIG. 6a is a chart depicting blood glucose content in a patient analyzed by a biochemical method.
Figure 6B:
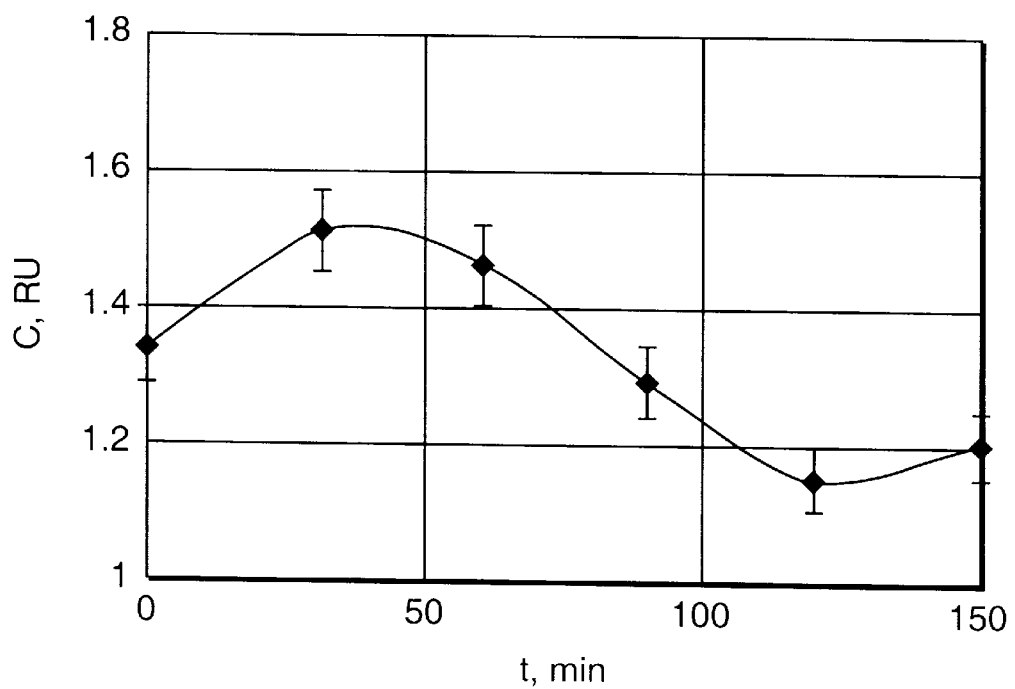
FIG. 6b is a chart depicting blood glucose content in the same patient analyzed using the present invention.

A preferred and exemplary embodiment of a noninvasive blood glucose analyzer is described in FIG. 1 and is represented generally by numeral 10. This analyzer includes a fiber optic component 20 constructed by combining several fiber bundles. Any fiber optic device that has high optical transmission in the wavelengths that glucose absorbs light may be used. In a most preferred embodiment, the fiber optic device is constructed from pure silica glass core fiber or doped silica glass core fiber, such as disclosed in U.S. Pat. Nos. 4,162,908 and 3,659,915, incorporated by reference herein.

At a first end face 22 of the fiber optic component, a light source 14 is placed. As a source a light, any pulsed light source, such as a photographic flash lamp, may be used. To increase the light energy projecting onto the first end face 22 from the light source 14, a reflector may be installed behind the source. In one embodiment, the reflector may be made from a polished metallic plate.

A control unit 12 switches on the light for a short period of time when the blood glucose analyzer is activated. The control unit controls the mode of operation and provides maximum stabilization of the radiation pulse.

Through a second end face 24 of the fiber optic component, light radiation is projected onto the investigated area of a patient's arm. The light signal reflected from internal tissue layers also passes through the second end face 24 of the fiber optic component. In a particularly preferred embodiment, the second end face 24 is constructed as a polished rectangular window (size is 15×12 mm), which protrudes from the surface of the fiber optic component.

The second end face 24 of the fiber optic component also leads to a test channel extension branch 26. At the end of this extension branch is a third end face 27 optically connected to a first system of light filters 30, which in turn are optically connected to a first photodetector 32. The first system of light filters 30 includes an interference filter that transmits a narrow bandwidth of light within the range of wavelengths that is absorbed by glucose. The first system of light filters 30 may also include a Germanium (Ge), Silicon (Si), or similar type optical filter to filter out the visible part of the spectrum.

In preferred embodiments, light transmitted through the interference filter is a range or wavelengths that is not substantially absorbed by other blood components, such as albumin, urea, or cholesterol. For example, light is absorbed by glucose but not absorbed substantially by other blood components in the range of wavelengths of between about 1550 nm and 1700 nm and between about 2050 nm and 2400 nm. See Heise, H. M., "Non-Invasive Monitoring of Metabolites Using Near Infrared Spectroscopy: State of the Art," *Hormone and Medical Research,* 28:527–534 (1996), incorporated by reference herein. In a most preferred embodiment, the interference filter transmits wavelengths within the range of wavelengths between about 2080 nm to 2200 nm.

The bandwidth of light transmitted through the interference filter should also be narrow enough to avoid interference from other components of blood, thereby improving the signal to noise ratio, which in turn improves accuracy and repeatability. In a most preferred embodiment, the interference filter transmits a bandwidth of light of about 20 nm or less.

Light passes through the first system of light filters to the first photodetector 32. Any photodiode having a spectral sensitivity in the range of the light transmitted through the light filters may be used as the photodetector. In a preferred embodiment, the photodiode has a spectral characteristic with a maximum sensitivity at the same wavelengths as the transmission band of the interference filter. In an exemplary embodiment, a solid state photodiode developed at Ioffe Physical-Technical Institute, St. Petersburg Russia (type FD-24-05) can be used. In this photodiode, the photosensitive surface area used is about 500 micrometer in diameter, the output rise and fall times are both near 1 microseconds, the spectral range is from 1800 to 2300 nm, the maximum response is in the range from 1950 to 2150 nm, and the electric current light sensitivity at 2000 nm is about 1.1 amperes/watt. Through a combination of the light filters and the photodetector, a supply of high spectral selectivity at the selected wavelength is provided.

The output of the first photodetector 32 is connected to a first pulse amplifier 34 that amplifies the electrical signals. In a preferred embodiment, the amplifier has a voltage amplification factor not less than $1 \times 10^6$, a high dynamic range with linear output up to 3–4 volts, a consumption of an electric current no more than 3 milliamperes on all stages of an amplifier, bandwidth up to several Megahertz, and noise level indicated on an amplifier input no more than 0.1 microvolts. In an exemplary embodiment, the amplifier can be constructed with a Russian operational amplifier of a type 1401UD2 in which three sequential stages of amplification (gain) with deep negative feedback are employed. The amplifier input is matched with output impedance of the photodetector. In preferred embodiments, the first stage of the amplifier is mounted as close to the photodetector as possible, and most preferably the photo sensor is combined on a chip with an amplifier, as in the TSL260 light-to-voltage sensors made by Texas Instruments. As a source of a two-polar power supply of the amplifier, in preferred embodiments, batteries with a low level of internal current noise can be used, which makes the amplifier significantly less sensitive to signal noise from the common circuits. To protect against external electromagnetic and electrostatic interference, the amplifier and photodetector can be placed in a steel cylindrical electromagnetic shield. In this preferred embodiment of the amplifier, the level of output voltage of the measured signal is equal to 3–4 volts and the level of output noise is approximately 0.01 volts, which results in a signal to noise ratio of 300–400:1.

The first amplifier output is connected to a first analog-to-digital converter 36. Because the measuring signal may have a small duration (about 20 microseconds) and an incorrect form, using direct conversion "voltage-code" can cause significant errors. Therefore, in a more preferred embodiment, a measuring signal of the incorrect form is converted into a rectangular pulse of greater duration (approximately several milliseconds) using the principle of preliminary latitude-pulse conversion. In this way, the duration of the given transformed rectangular pulse is proportional to common energy of an input signal. This rectangular pulse of variable duration is filled in with pulses of the standard generator. The binary counter calculates the quantity of these standard pulses and produces, as the output of the analog-digital converter, a binary code having a value proportional to energy of the measured signal. This binary code, which indicates the strength of light signal of the test channel, can then be entered into a microprocessor 50. The system may also provide for memory back-up through a secondary power supply, which allows for battery replacement during routine maintenance when one battery no longer meets the voltage requirements for system operation.

As a whole, the first system of light filters 30, first photodetector 32, first amplifier 34, and first analog-to-digital converter 36 comprise the test channel. Through this channel, a measurement is obtained of the intensity of light reflected from the tissues of the patient and illuminating the second end face 24 of the fiber optic component.

The first end face 22 of the fiber optic component also has a reference channel extension branch 28. This extension branch has a fourth end face 29 optically connected to a second system of light filters 40, which in turn are optically connected to a second photodetector 42. The output of the photodetector is connected to a second amplifier 44, which in turn is connected to a second analog-to-digital converter 46. The output of the analog-to digital converter, a binary code indicating the strength of the light signal of the reference channel, can then also be entered into the microprocessor 50. The second system of light filters 40, second photodetector 42, second amplifier 44, and second analog-to-digital converter 46 are identical to the first system of light filters 30, first photodetector 32, first amplifier 34, and first analog-to-digital converter 36 of the test channel.

As a whole, the second system of light filters 40, second photodetector 42, second amplifier 44, and second analog-to-digital converter 46 comprise the reference channel. Through this channel, a measurement is obtained of the intensity of light that is transmitted to the skin and tissues of the patient, which serves as a reference for comparison to the light reflected from the patient.

In operation, a preferred method for measuring glucose concentration, using the apparatus described above, is as follows. After turning on the analyzer, an indicator light indicates readiness to start the measurements. The inner side of the wrist of the left or right arm of the patient is firmly placed against the window of the second end face 24 of the fiber optic component. After pressing a "START" button, a light pulse from the light source 14 passes through the fiber optic component 20, without filtering, and out the second end face 24, illuminating an investigated site of the patient. The light pulse passes through the skin, tissues, and vessels, is partially absorbed by glucose in the blood, and is partially reflected from tissues, internal walls of the vessels, bone surfaces. Reflected light returns to the second end face 24 and is registered in the test channel. In the channel, measurement is made of a preset wavelength of the reflected light, such as 2120 nm (the wavelength at which glucose absorbs the most light), by selecting the light filters 30 and photodetector 32 to optimize detection at the preset wavelength. The signal from a photodetector is magnified by an amplifier 34, converted to a digital code with the help of an analog-digital converter 36, and entered into the memory of the microprocessor 50. Simultaneously, a portion of light radiation from the light source passes into the reference channel, is measured, and also entered into the memory of the microprocessor. This digital data of the reference channel is used to normalize the measurements of reflected light obtained from measuring channel and, thereby, eliminates errors due to instability in the light signal.

The microprocessor can also account for matching calibration factors and corrections, which are individual for each patient. Although the reflected light signal is always proportional to the patient's glucose concentration, the intensity of the signal for a given concentration will vary from patient to patient due to individual characteristics such as body fat, skin thickness, and blood vessel location. Consequently, to measure glucose concentration in absolute units (e.g., millimole/liter or milligram/deciliter), these characteristics must be taken into consideration. In a preferred embodiment, patients can be given a glucose test during which various glucose concentrations are measured using both biochemical methods (drawing blood) and the photometric method of the present invention. This information can then be used to calibrate the microprocessor so that measurements obtained by the photometric method of the present invention can be converted to absolute units. The microprocessor can then output the value of glucose concentration in absolute units, which can be shown on a display board of the instrument 52.

In an alternative embodiment, the light source can emit a narrow bandwidth of light, thereby reducing or eliminating the need for passing the reflected light through light filters. For example, the light source can be a laser diode emitting a bandwidth of light of about 20 nm or less within the range of wavelengths between about 2080 nm to 2200 nm. In such a case, the intensity of the reflected light can be measured directly by the first photodetector, and the light from the light source passing through the reference channel can be measured directly by the second photodetector, without passing either the reflected light or the reference channel light through a system of light filters. In all other respects, the operation of this embodiment of the invention is similar to the operation of the invention using the broad band light source and light filters as described above.

The invention will be further clarified by the following examples, which are intended to be purely exemplary of the invention.

EXAMPLES

A prototype of the present invention has been tested at the Sokolov Central Hospital (a member of PREMIER, Inc.) in St. Petersburg, Russia. To check the accuracy of the prototype, results obtained from the noninvasive blood glucose analyzer were compared to results obtained by biochemical analysis of the blood of patients using a well-known medical diagnostic method for obtaining a "sugar curve." A blood sample was taken from the finger of a fasting patient, after which the patient drank 200 grams of a strong glucose solution. Every 30 minutes afterwards for 2.5 hours, additional blood samples were drawn. The blood samples were then biochemically analyzed for glucose concentration, and the six data points were used to construct a "sugar curve."

Immediately before blood was drawn from the patients for the biochemical analysis, measurements were taken using the non-invasive glucose monitor of the present invention. The wrist of the patient was positioned adjacent the window of the optical fiber, and several measurements were taken over a period of 1.5 to 2 minutes. Results for both the measuring channel and the reference channel were averaged.

The level of sugar in the blood according to data from our prototype was determined in relative units by dividing the results of the reference channel by the results of the test channel. This data was then used to construct a graph of the obtained results against time. The data from the biochemical analysis was also used to construct a graph of glucose concentration in the blood against time. A comparison of the results was then conducted.

The results of biochemical and optical measurements of sugar in the blood of 5 patients are given in FIGS. 2–6. Comparing the relative values of glucose concentration for these patients demonstrates a close correlation between the "sugar curves" using biochemical measurements and using the optical measurements using the non-invasive glucose monitor of the present invention. These results validate the utility of the apparatus and method of the present invention to measure blood glucose concentration noninvasively.

These tests also revealed that the following principles are important to the construction and operation of the apparatus of the present invention. Inconsistency of the position of the measuring place on a wrist in relation to the second end face of the optical fiber component can increase the error. Even a small displacement of a position of the wrist in relation to a measuring platform causes significant change to the measurements obtained on the measuring channel. In addition, results are influenced by the pressure of wrist against the second end face. To overcome these problems, the measuring platform must be designed to reduce these variables. For example, a long flexible fiber cable will enable the second end face to be fixed in a position on the wrist. The device may also incorporate a pressure plate and pressure sensors to facilitate uniform usage by the patient and insure proper measurement.

In addition, because the level of the signal from the photodetector is very small, the amplifier should have a sufficiently large amplification factor and low noise level to ensure normal operation of the analog-to-digital converter. Moreover, because the noise of the amplifier and photo diode leads to a large spread of the indications, the ratio of a signal to noise of the amplifier should be increased at least 10 times. In the prototype used in the examples, the ratio of a signal to noise was about 300 having an output signal of 3 volts and a noise level of 0.01 volts. Better results could be obtained with the dynamic range of an amplifier having linear output up to 5 volts at a noise level up to 0.01 volts, producing a signal to noise ratio of about 500.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An apparatus for noninvasively measuring the glucose concentration in the blood of a patient, comprising;
   (a) a light source,
   (b) a test channel comprising (i) a first light filter capable of transmitting a narrow bandwidth of light within a range of wavelengths that is absorbed by glucose, (ii)

a first photodetector capable of measuring the light passing the light filter, (iii) a first pulse amplifier, and (iv) a first analog-to-digital converter, (c) a first optic unit comprising optical fibers and capable of transporting light pulses from the light source to the skin of a patient, receiving light reflected back from the patient, and transporting the reflected light to the test channel, (d) a reference channel comprising (i) a second light filter, (ii) a second photodetector, (iii) a second pulse amplifier, and (iv) a second analog-to-digital converter, each identical to the corresponding elements in the test channel, (e) a second optic unit capable of transporting light pulses from the light source to the reference channel, and (f) a processing unit capable of comparing the output of the test channel to the output of the reference channel to quantify the intensity of light absorbed by the glucose in the blood of the patient.

2. The apparatus of claim 1, wherein the first and second light filters are capable of transmitting light having a bandwidth of about 20 nm or less.

3. The apparatus of claim 2, wherein the first and second light filters are capable of transmitting light within a range of wavelengths of between about 2080 nm to 2200 nm.

4. The apparatus of claim 3, wherein the optical fibers comprise pure silica glass core fibers or doped silica glass core fibers.

5. An apparatus for noninvasively measuring the glucose concentration in the blood of a patient, comprising:

(a) a light source, (b) a light filter capable of transmitting a narrow bandwidth of light within a range of wavelengths that is absorbed by glucose, (c) a first optic unit comprising optical fibers and capable of transporting light pulses from the light source to the skin of a patient, receiving light reflected back from the patient, and transporting the reflected light to the light filter, (d) a second optic unit capable of transporting light pulses directly from the light source to the light filter, (e) a photodetector capable of measuring the light passing the light filter, (f) a processing unit capable of comparing the intensity of the reflected light passing through the light filter to the intensity of the light directly from the light source to quantify the intensity of light absorbed by the glucose in the blood of the patient.

6. The apparatus of claim 5, wherein the light filter is capable of transmitting light having a bandwidth of about 20 nm or less.

7. The apparatus of claim 6, wherein the light filter is capable of transmitting light within a range of wavelengths of between about 2080 nm to 2200 nm.

8. The apparatus of claim 5, wherein the optical fibers comprise pure silica glass core fibers or doped silica glass core fibers.

9. A method for noninvasively measuring the glucose concentration in the blood of a patient, comprising:

(a) projecting a pulse of light through a fiber optic device placed in direct contact with the patient's skin, (b) measuring the intensity of light reflected from the patient over a narrow bandwidth within a range of wavelengths that is absorbed by glucose, (c) measuring the intensity of light projected onto the patient's skin over the same bandwidth and wavelengths used in step (b), and (d) comparing the measurements of light obtained in steps (b) and (c) to quantify the intensity of light absorbed by the glucose in the blood of the patient.

10. The method of claim 9, wherein the bandwidth of light measured in steps (b) and (c) is about 20 nm or less.

11. The method of claim 10, wherein the reflected light measured in steps (b) and (c) is within a range of wavelengths of between about 2080 nm to 2200 nm.

12. The method of claim 9, wherein the light projected onto the patient's skin has a narrow bandwidth and is within a range of wavelengths that is absorbed by glucose.

13. The method of claim 9, wherein the light projected onto the patient's skin has a bandwidth of about 20 nm or less.

14. The method of claim 13, wherein the light projected onto the patient's skin is within a range of wavelengths of between about 2080 nm and 2200 nm.

15. The method of claim 14, wherein the light projected onto the patient's is emitted from a laser diode.

16. The method of claim 9, wherein the light projected through the fiber optic device is not wavelength or intensity modulated.

17. A method for noninvasively measuring the glucose concentration in the blood of a patient, comprising:

(a) generating a pulse of light, (b) projecting a first portion of the pulse of light through a fiber optic device placed in direct contact with the patient's skin, (c) passing the light reflected from the patient through a first light filter that transmits a narrow bandwidth of light within a range of wavelengths that is absorbed by glucose, (d) passing a second portion of the pulse of light through a second light filter identical to first light filter, (e) measuring the intensity of the light passing through the first and second light filters, and (f) comparing the intensity of light passing through the first light filter to the intensity of light passing through the second light filter to quantify the intensity of light absorbed by the glucose in the blood of the patient.

18. The method of claim 17, wherein the first and second light filters transmit light having a bandwidth of about 20 nm or less.

19. The method of claim 18, wherein the first and second light filters transmit light within a range of wavelengths of between about 2080 nm to 2200 nm.

20. The method of claim 19, wherein the fiber optic device is placed on the lateral side of the patient's ear lobe and a reflective device is placed on the medial side of the patient's ear lobe.

* * * * *

UNITED STATES PATENT AND TRADEMARK OFFICE
CERTIFICATE OF CORRECTION

PATENT NO. : 6,097,975
DATED : August 1, 2000
INVENTOR(S) : Petrovsky et al.

It is certified that error appears in the above-identified patent and that said Letters Patent is hereby corrected as shown below:

Column 8,
Line 67, "that is absorbed by glucose" should read -- of between 2050 nm to 2400 nm --.

Column 9,
Lines 34-35, "that is absorbed by glucose" should read -- of between 2050 nm to 2400 nm --.
Line 57, "claim 5" should read -- claim 7 --.

Column 10,
Line 5, "that is absorbed by glucose" should read -- of between 2050 nm to 2400 nm --.
Line 27, "patient's" should read -- patient's skin --.
Lines 40-41, "that is absorbed by glucose" should read -- of between 2050 nm to 2400 nm --.

Signed and Sealed this

Twenty-third Day of July, 2002

*Attest:*

JAMES E. ROGAN
*Attesting Officer*   *Director of the United States Patent and Trademark Office*